United States Patent [19]

Kummer et al.

[11] Patent Number: 5,769,278
[45] Date of Patent: Jun. 23, 1998

[54] ADJUSTABLE MEASURED DOSE DROPPER

[76] Inventors: Frederick J. Kummer, 344 82nd St., Brooklyn, N.Y. 11209; Victor H. Frankel, 39 Gramercy Park, New York, N.Y. 10010

[21] Appl. No.: 721,457

[22] Filed: Sep. 27, 1996

[51] Int. Cl.$^6$ ....................................................... B67D 5/38
[52] U.S. Cl. .......................... 222/158; 222/308; 222/422; 141/24
[58] Field of Search ..................................... 222/422, 420, 222/304, 308, 158; 141/23, 24; 604/298

[56] References Cited

U.S. PATENT DOCUMENTS

| | | | |
|---|---|---|---|
| 1,422,778 | 7/1922 | Petcher | 141/24 |
| 2,129,144 | 9/1938 | Lancaster | 141/23 |
| 5,249,711 | 10/1993 | Filbert, Jr. | 222/420 X |
| 5,514,118 | 5/1996 | Kummer et al. | 222/450 X |

*Primary Examiner*—Gregory L. Huson
*Attorney, Agent, or Firm*—Stephen C. Glazier; Pillsbury Madison & Sutro, LLP

[57] ABSTRACT

A measured dose dropper includes an adjustable extension fitted within a hollow barrel in an end opposite that of the opening of the barrel. The adjustable extension includes gradation marks which correspond to the volume within the hollow barrel as adjusted by sliding the adjustable extension. A float within the hollow barrel acts as a float valve when fluid is drawn into the hollow barrel, preventing no more than the desired precise amount of fluid to be contained within the hollow barrel. Accordingly, an adjustable measured dose of fluid can be reliably and accurately dispensed.

28 Claims, 1 Drawing Sheet

ADJUSTABLE MEASURED DOSE DROPPER

BACKGROUND OF THE INVENTION

1. Field of the Invention

The present invention relates to an adjustable measured dose dropper, and more particularly, to an eye dropper which is capable of adjustability to reliably dispense an accurate and specific amount of fluid.

2. Description of the Related Art

A measured dose dropper is disclosed in U.S. Pat. No. 5,514,118, issued May 7, 1996, the contents of which are incorporated herein by reference. Although the invention disclosed in U.S. Pat. No. 5,514,118 dramatically advances the state of the art of droppers, and particularly eye droppers, only a single predetermined dose can be dispensed. Accordingly, there remains a need for a measured dose dropper which is capable of variably adjusting the amount of the fluid dose dispensed. The present invention fulfills this need.

SUMMARY OF THE INVENTION

An object of the present invention is to provide a measured dose dropper which is able to accurately dispense a fluid in variably adjustable amounts.

To fulfill this and other objects, the measured dose dropper according to the present invention includes an adjustable extension fitted within a hollow barrel in an end opposite that of the opening of the barrel. The adjustable extension includes gradation marks which correspond to the volume within the hollow barrel as adjusted by sliding the adjustable extension. A float within the hollow barrel acts as a float valve when fluid is drawn into the hollow barrel, preventing no more than the desired precise amount of fluid to be contained within the hollow barrel. Accordingly, an adjustable measured dose of fluid can be reliably and accurately dispensed.

It is an object of the pipette embodiment of the present invention to provide a very accurate and easy to use pipette that is safer than a normal pipette when used in the oral suction manner with dangerous fluids, by eliminating the possibility of sucking the fluid into the mouth.

BRIEF DESCRIPTION OF THE DRAWINGS

The present invention will be clearly understood in light of the following detailed description in conjunction with the attached drawings, in which.

DETAILED DESCRIPTION OF THE PREFERRED EMBODIMENTS

Figure 1:
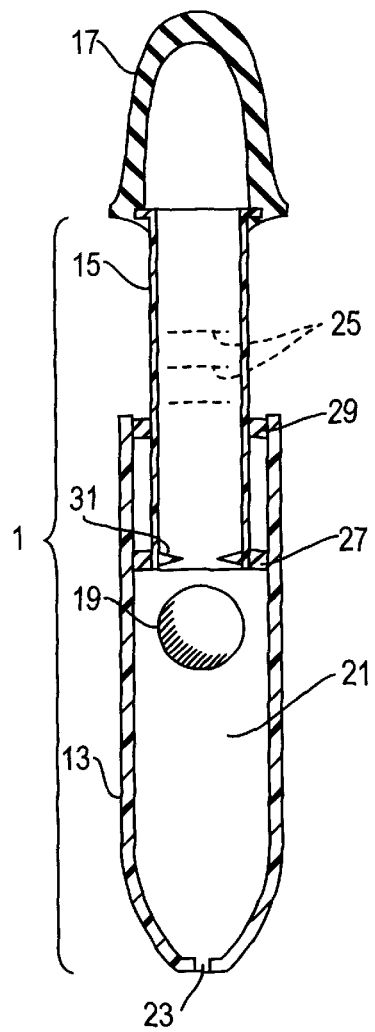
FIG. 1 is a cutaway drawing of an adjustable dropper according to a preferred embodiment of the present invention.

An adjustable measured dose eyedropper according to one preferred embodiment of the present invention is illustrated in FIG. 1. It includes a barrel assembly 11, including a hollow barrel 13 and a hollow adjustable extension 15, a squeeze bulb 17 attached to one end of the adjustable extension 15, and a float 19 within the barrel 13. The barrel and extension may be made of plastics such as polyethylene and styrene, for example, or they may be made of glass or even metal. However, transparent material is preferred.

The inner surfaces of the hollow barrel 13 and adjustable extension 15 together form an inner chamber 21 of the barrel assembly 11 which communicates with an opening 23 at one end of the barrel 13. Preferably, the adjustable extension 15 fits within the barrel 13 to form an airtight seal for the inner chamber 21. Furthermore, the adjustable extension 15 slides with respect to the hollow barrel 13. As should be readily apparent, as the adjustable extension 15 slides with respect to the hollow barrel 13, the volume of the inner chamber 21 is either compressed or expanded, and in particular, the volume of the portion of the barrel 13 between the opening 23 and the adjustable extension 15 is either compressed or expanded. This portion is measured and is indicated by gradation marks 25, preferably etched or printed on an outer surface of the adjustable extension 15.

The float 19 has outer dimensions greater than the inner dimensions of the adjustable extension 15 and the dimensions of the opening 23. Alternatively, there may be provided an annular ring 31 formed within the adjustable extension 15 which sufficiently projects from the inner surface of the adjustable extension 15 such that inner dimensions thereof are less than the outer dimensions of the float 19. The float 19 is made from a material which has a density less than most fluids, and it may even be hollow, so that the float 19 floats in most fluids. Preferably, the float is made of polypropylene plastic or like plastic.

Attached around the end of the adjustable extension 15 which inserts inside hollow barrel 13, is a polyrene or rubber compressible O-ring or gasket 27, the dimensions of which being such that the adjustable extension 15 snugly fits within the hollow barrel 13 to form an airtight seal. However, the gasket 27 is made of a sufficiently deformable material such that the adjustable extension 15 can be slidably positioned with respect to the hollow barrel 13 without difficulty. Moreover, the inside of the end of the hollow barrel 13 which inserts over the extension 15, may also be fitted with a O-ring or gasket 29. Not only does the gasket 29 improve the airtightness of the seal between the adjustable extension 15 and the hollow barrel 13, but the gaskets 27 and 29 also cooperate to prevent the adjustable extension 15 from being separated from the hollow barrel 13.

Alternatively, the function of the O-rings 27 and 29, may be performed by annular rings of about the same size, location, and dimension that are integral features of the extension 15 or barrel 13, respectively. This is further shown and discussed regarding FIG. 3.

The measured dose dropper illustrated in FIG. 1 operates as follows. First, the amount of the dose to be dispensed is adjusted by sliding the adjustable extension 15 until the desired gradation mark 25 lines up with a permanent reference point, preferably the end of the hollow barrel 13 near O-ring 29. The gradation marks 25 may be separated in standard volume units, such as every 0.5 milliliters. When the desired gradation mark 25 is properly aligned by sliding the adjustable extension 15, the volume of the space in the hollow barrel 13 between the opening 23 and the bottom of the adjustable extension 15, less the volume of float 19, corresponds to the amount signified by the desired gradation mark 25. Next, the fluid to be dispensed is drawn into the hollow barrel 13 by squeezing the squeeze bulb 17 to expel air, immersing the opening 23 of hollow barrel 13 into a container of the fluid, and releasing the squeeze bulb 17. The suction created by the release of the squeeze bulb 17 causes the fluid to be drawn into the hollow barrel 13. Because the float 19 has a lower density than the fluid, the float 19 floats on top of the fluid as it is drawn into the hollow barrel 13. When the exact amount of fluid has been drawn, the float 19 acts as a float valve by lodging against the bottom of the adjustable extension 15, and preventing more fluid from being drawn into barrel 13.

Figures 2, 3:
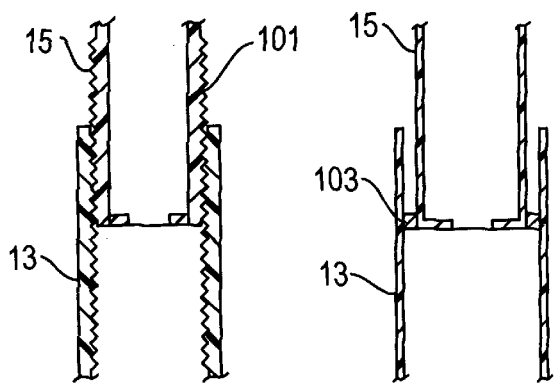
FIG. 2 is a cutaway drawing showing a portion of an adjustable dropper having a threaded fit adjustable barrel extension according to a second preferred embodiment of the present invention.
FIG. 3 is a cutaway drawing showing a portion of an adjustable dropper having an interference fit adjustable barrel extension according to a third preferred embodiment of the present invention.

FIG. 2 illustrates a second preferred embodiment of the present invention. In this embodiment, threads 101 are formed on the outer surface of the adjustable extension 15 and an inner surface of the hollow barrel 13. The measured dose is thereby adjusted by screwing the extension 15 either into or out of the hollow barrel 13. This arrangement provides a reliable airtight seal and a stable positioning of the adjustable extension 15.

FIG. 3 illustrates a third preferred embodiment of the present invention. In this embodiment, an annular ring 103 is formed around an end of adjustable extension 15 and projecting from the outer surface of the extension 15 such that its outer diameter is equal to or slightly greater than the inner diameter of the hollow barrel 13, providing an interference fit between the two components.

Figures 4, 5:
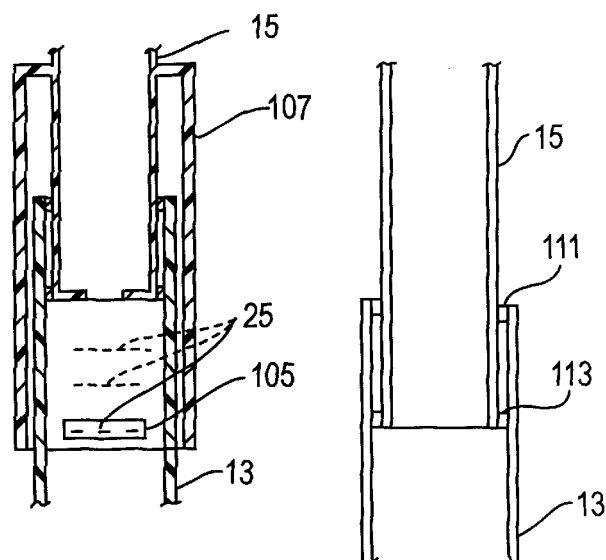
FIG. 4 is a drawing of an adjustable dropper with a dose indicator shroud according to any of the preferred embodiments of the present invention.
FIG. 5 illustrates an alternative means for preventing the adjustable extension from being separated from the hollow barrel, in one embodiment.

FIG. 4 illustrates a dose indicating shroud 107 that may be used with any of the first through third preferred embodiments of the present invention. The shroud is attached to the barrel extension 15 so that it moves when the extension is adjusted. Preferably, the shroud is transparent. In this alternative embodiment, the gradation marks 25 are etched or painted on the outer surface of the barrel 13 and the dose is measured by aligning the corresponding gradation mark with an indicator 105 which is etched on the surface of the shroud.

FIG. 5 illustrates an alternative means for preventing the adjustable extension 15 from being separated from the hollow barrel 13. In this embodiment, molded tabs are provided both on the adjustable extension 113 and the hollow barrel 111. These tabs do not necessarily extend completely around the entire circumference of the extension and the hollow barrel, but cooperate sufficiently to prevent their separation.

Although the present invention has been described hereinabove with reference to the preferred embodiments thereof, those skilled in the art will readily appreciate that various substitutions and modifications can be made thereto without departing from the spirit and scope of the present invention as set forth in the appended claims.

The terms "dropper" and "eye dropper" are defined herein to have the same meaning as "eye dropper" as defined in the specification of U.S. Pat. No. 5,514,118 issued May 7, 1996, to Kummer et al., at column 3, lines 31–44.

A measured dose eye dropper is the preferred embodiment of the present invention shown herein in the figures and described in detail. However, the present invention can be embodied in any other dropper or eye dropper form, including, without limitation, pipettes.

The present invention is shown with a spherical float 19 in FIG. 1, however, any of a variety of float shapes may be used in the present invention, including without limitation any of the float shapes shown in U.S. Pat. No. 5,514,118.

In the pipette embodiment of the present invention, when used in the oral suction manner, the possibility of sucking dangerous fluids into the mouth is eliminated, since the action of the float 19 prevents the measured fluid from flowing past the float 19. This happens when the float 19 floats up to abut the annular ring 31, and stops additional fluid from being drawn into the device. This same action also stops any fluid from being drawn past the float 19 towards the mouth in a pipette embodiment.

What is claimed is:

1. A measured dose dropper comprising:
 (a) a hollow barrel having an inner chamber, a first end, and a second end opposite said first end, said first end having a fluid opening and said second end having an extension opening, both said fluid opening and said extension opening communicating with said inner chamber;
 (b) a barrel extension adapted to be received in said extension opening of said hollow barrel, said barrel extension also being hollow and having a first end and a second end opposite said first end, said first end having a barrel opening with an inner diameter and said second end having a suction opening;
 (c) means for adjustably securing said barrel extension to said second end of said hollow barrel such that said barrel opening of said barrel extension communicates with said inner chamber of said hollow barrel, the space between said first end of said barrel extension and said first end of said hollow barrel defining a volume of said inner chamber, said volume being adjusted by moving said barrel extension with respect to said hollow barrel;
 (d) means for providing suction to draw a fluid into said inner chamber, said second end of said barrel extension being adapted to communicate with said means for providing suction, said fluid opening of said hollow barrel being adapted to permit passage of said fluid; and
 (e) a float with an outer diameter greater than said inner diameter of said barrel opening of said barrel extension, said float being disposed in said inner chamber of said hollow barrel between said barrel opening of said barrel extension and said fluid opening of said hollow barrel, said float having a density which is less than a density of said fluid so that when said fluid is drawn into said inner chamber, said float floats against said barrel opening of said barrel extension and prevents more than said volume of said fluid, less the volume of said float, from being drawn into said inner chamber.

2. The invention in claim 1, further comprising dose indicating means for denoting measured volumes corresponding to said volume of said inner chamber, less the volume of said float.

3. The invention in claim 2, wherein said dose indicating means includes a set of gradation marks on visible portions of said barrel extension.

4. The invention in claim 2, wherein said dose indicating means includes a shroud which is fixably attached to said barrel extension and a set of gradation marks on visible portions of said hollow barrel.

5. The invention in claim 1, wherein said adjustably securing means is an O-ring disposed between an outer surface of said barrel extension and an inner surface of said hollow barrel.

6. The invention in claim 1, wherein said adjustably securing means is a mating pair of threads formed on an outer surface of said barrel extension and an inner surface of said hollow barrel.

7. The invention in claim 1, wherein said adjustably securing means is an interference fit annular ring disposed between an outer surface of said barrel extension and an inner surface of said hollow barrel.

8. The invention in claim 1, wherein said adjustably securing means is a mating pair of molded tabs formed on an outer surface of said barrel extension and an inner surface of said hollow barrel.

9. The invention in claim 1, wherein said suction providing means is a squeeze bulb.

10. The invention in claim 1, wherein said hollow barrel and said barrel extension both have a cylindrical shape.

11. The invention in claim 1, further comprising means for filling space between an outer surface of said barrel extension and an inner surface of said hollow barrel so as to provide an airtight fit between said barrel extension and said hollow barrel.

12. The invention in claim 1, wherein said adjustably securing means also provides an airtight fit between said barrel extension and said hollow barrel.

13. An improved measured dose dropper having:
(a) a hollow barrel having a first end and a second end opposite said first end, and an inner chamber;
(b) means for providing suction to draw a fluid into said inner chamber of said hollow barrel, said hollow barrel having a fluid opening at said first end which is adapted to permit passage of said fluid; and
(c) a float with an outer diameter disposed within said inner chamber and having a density which is less than a density of said fluid;
the improvement comprising:
(a) a barrel extension adapted to be received in an extension opening at said second end of said hollow barrel, said barrel extension also being hollow and having a first end and a second end opposite said first end, said first end having a barrel opening with an inner diameter less than said outer diameter of said float, and said second end having a suction opening which is adapted to communicate with said suction providing means; and
(b) means for adjustably securing said barrel extension to said second end of said hollow barrel such that said barrel opening of said barrel extension communicates with said inner chamber of said hollow barrel, the space between said first end of said barrel extension and said first end of said hollow barrel defining a volume of said inner chamber, said volume being adjusted by moving said barrel extension with respect to said hollow barrel, so that when said fluid is drawn into said inner chamber, said float floats against said barrel opening of said barrel extension and prevents more than said volume of said fluid, less the volume of said float, from being drawn into said inner chamber.

14. The invention in claim 13, the improvement further comprising dose indicating means for denoting measured volumes corresponding to said volume of said inner chamber, less the volume of said float.

15. The invention in claim 14, wherein said dose indicating means includes a set of gradation marks on visible portions of said barrel extension.

16. The invention in claim 14, wherein said dose indicating means includes a shroud which is fixably attached to said barrel extension and a set of gradation marks on visible portions of said hollow barrel.

17. The invention in claim 13, wherein said adjustably securing means is an O-ring disposed between an outer surface of said barrel extension and an inner surface of said hollow barrel.

18. The invention in claim 13, wherein said adjustably securing means is a mating pair of threads formed on an outer surface of said barrel extension and an inner surface of said hollow barrel.

19. The invention in claim 13, wherein said adjustably securing means is an interference fit annular ring disposed between an outer surface of said barrel extension and an inner surface of said hollow barrel.

20. The invention in claim 13, wherein said adjustably securing means is a mating pair of molded tabs formed on an outer surface of said barrel extension and an inner surface of said hollow barrel.

21. The invention in claim 13, wherein said suction providing means is a squeeze bulb.

22. The invention in claim 13, wherein said hollow barrel and said barrel extension both have a cylindrical shape.

23. The invention in claim 13, the improvement further comprising means for filling space between an outer surface of said barrel extension and an inner surface of said hollow barrel so as to provide an airtight fit between said barrel extension and said hollow barrel.

24. The invention in claim 13, wherein said adjustably securing means also provides an airtight fit between said barrel extension and said hollow barrel.

25. The invention in claim 1, wherein said means for providing suction includes an end adapted for oral suction.

26. The invention in claim 13, wherein said means for providing suction includes an end adapted for oral suction.

27. A measured dose dropper comprising:
(a) a hollow barrel having an inner chamber, a first end, and a second end opposite said first end, said first end having a fluid opening and said second end having an extension opening, both said fluid opening and said extension opening communicating with said inner chamber;
(b) a barrel extension adapted to be received in said extension opening of said hollow barrel, said barrel extension also being hollow and having a first end and a second end opposite said first end, said first end having a barrel opening with an inner diameter and said second end having a suction opening;
(c) means for adjustably securing said barrel extension to said second end of said hollow barrel such that said barrel opening of said barrel extension communicates with said inner chamber of said hollow barrel, the space between said first end of said barrel extension and said first end of said hollow barrel defining a volume of said inner chamber, said volume being adjusted by moving said barrel extension with respect to said hollow barrel;
(d) said second end of said barrel extension being open and adapted to the application of oral suction, said fluid opening of said hollow barrel being adapted to permit passage of said fluid; and
(e) a float with an outer diameter greater than said inner diameter of said barrel opening of said barrel extension, said float being disposed in said inner chamber of said hollow barrel between said barrel opening of said barrel extension and said fluid opening of said hollow barrel, said float having a density which is less than a density of said fluid so that when said fluid is drawn into said inner chamber, said float floats against said barrel opening of said barrel extension and prevents more than said volume of said fluid, less the volume of said float, from being drawn into said inner chamber.

28. An improved measured dose dropper having:
(a) a hollow barrel having a first end and a second end opposite said first end, and an inner chamber;
(b) said hollow barrel having a fluid opening at said first end which is adapted to permit passage of said fluid; and (c) a float with an outer diameter disposed within said inner chamber and having a density which is less than a density of said fluid;

the improvement comprising:

(a) a barrel extension adapted to be received in an extension opening at said second end of said hollow barrel, said barrel extension also being hollow and having a first end and a second end opposite said first end, said first end having a barrel opening with an inner diameter less than said outer diameter of said float, and said second end having a suction opening which is adapted to the application of oral suction; and (b) means for adjustably securing said barrel extension to said second end of said hollow barrel such that said barrel opening of said barrel extension communicates with said inner chamber of said hollow barrel, the space between said first end of said barrel extension and said first end of said hollow barrel defining a volume of said inner chamber, said volume being adjusted by moving said barrel extension with respect to said hollow barrel, so that when said fluid is drawn into said inner chamber, said float floats against said barrel opening of said barrel extension and prevents more than said volume of said fluid, less the volume of said float, from being drawn into said inner chamber.

* * * * *